US 6,749,626 B1

(12) United States Patent
Bhat et al.

(10) Patent No.: US 6,749,626 B1
(45) Date of Patent: Jun. 15, 2004

(54) ACTINOMYCIN D FOR THE TREATMENT OF VASCULAR DISEASE

(75) Inventors: Vinayak D. Bhat, Sunnyvale, CA (US); Daryush Mirzaee, Sunnyvale, CA (US); Evgenia Mandrusov, Campbell, CA (US); Syed F. A. Hossainy, Fremont, CA (US); Deborra Sanders-Millare, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 284 days.

(21) Appl. No.: 09/715,510

(22) Filed: Nov. 17, 2000

Related U.S. Application Data

(63) Continuation-in-part of application No. 09/540,241, filed on Mar. 31, 2000.

(51) Int. Cl.[7] .................................................. A61F 2/06
(52) U.S. Cl. ........................ 623/1.1; 623/194; 623/195; 623/198
(58) Field of Search ........................... 606/194, 195, 606/198; 623/1.1, 1.42, 1.43, 1.21, 1.46; 424/422, 423, 426, 486

(56) References Cited

U.S. PATENT DOCUMENTS

| | | | |
|---|---|---|---|
| 2,072,303 A | 3/1937 | Herrmann et al. | 128/335.5 |
| 4,977,901 A | 12/1990 | Ofstead | 128/772 |
| 5,328,471 A | 7/1994 | Slepian | 604/101 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,628,730 A | 5/1997 | Shapland et al. | 604/21 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,800,392 A | 9/1998 | Racchini | 604/96 |

(List continued on next page.)

FOREIGN PATENT DOCUMENTS

| | | |
|---|---|---|
| EP | 0 301 856 | 2/1989 |
| EP | 0 665 023 | 8/1995 |
| WO | WO 96/40174 | 12/1996 |
| WO | WO 97/45105 | 12/1997 |
| WO | WO 99/01118 | 1/1999 |
| WO | WO 99/63981 | 12/1999 |
| WO | WO 00/02599 | 1/2000 |
| WO | WO 00/12147 | 3/2000 |
| WO | WO 00/64506 | 11/2000 |

OTHER PUBLICATIONS

Shozo Miyazaki, et al.; *Antitumor Effect of Implanted Ethylene–Vinyl Alcohol Copolymer Matrices Containing Anticancer Agents on Ehrlich Ascites Carcinoma and P388 Leukemia in Mice*; 1985; Chem. Pharm. Bull. vol. 33, No. 6, pp. 2490–2498.

Peter Barath, M.D. et al.; *Low Dose of Antitumor Agents Prevents Smooth Muscle Cell Proliferation After Endothelial Injury*; Feb. 1989; JACC vol. 13, No. 2, p. 252 A.

Yuji Matsumaru et al.; *Embolic Materials For Endovascular Treatment Of Cerebral Lesions*; 1997; J. Biomater. Sci. Polymer Edn. vol. 8, No. 7, pp. 555–569.

Shigeno, *Prevention of Cerebral Spasm by Bosentan, Novel Endothelin Receptor*; Chemical Abstract 125:212307 (1996).

*Primary Examiner*—Danny Worrell
(74) *Attorney, Agent, or Firm*—Squire, Sanders & Dempsey L.L.P.

(57) ABSTRACT

A composition, comprising actinomycin D, is locally or systemically administered for the treatment of a blood vessel, such as caused by recurring stenosis or restenosis following vascular trauma or disease.

28 Claims, 3 Drawing Sheets

U.S. PATENT DOCUMENTS

| | | | |
|---|---|---|---|
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,010,530 A | 1/2000 | Goiceochea | 623/1 |
| 6,015,541 A | 1/2000 | Greff et al. | 424/1.25 |
| 6,096,070 A | 8/2000 | Ragheb et al. | 623/1 |
| 6,153,252 A | 11/2000 | Hossainy et al. | 427/2.3 |
| 6,165,212 A | 12/2000 | Dereume et al. | 623/1.13 |
| 6,258,121 B1 | 7/2001 | Yang et al. | 623/1.46 |

ACTINOMYCIN D FOR THE TREATMENT OF VASCULAR DISEASE

CROSS-REFERENCE

This is a continuation-in-part of U.S. patent application Ser. No. 09/540,241 filed on Mar. 31, 2000.

BACKGROUND OF THE INVENTION

1. Field of the Invention

The invention relates generally to a therapeutic composition and introduction of the composition to certain target cell populations in a vascular region, such as smooth muscle cells, requiring modulation to ameliorate a diseased state, particularly for the treatment of stenosis or restenosis following a vascular trauma or disease. More particularly, the invention relates to methods of local and systemic administration of actinomycin D for the treatment of a vascular disease such as restenosis.

2. Description of the Background

Percutaneous transluminal coronary angioplasty (PTCA) is widely used as the primary treatment modality in many patients with coronary artery disease. PTCA can relieve myocardial ischemia in patients with coronary artery disease by reducing lumen obstruction and improving coronary flow. Recurrent stenosis or restenosis, characterized by the reocclusion of the coronary arteries following PTCA, remains a significant problem, however. Occurrence of immediate occlusion or development of restenosis within 6 months after the procedure results in significant morbidity and mortality or frequently necessitates further interventions such as repeat angioplasty or coronary bypass surgery.

The processes responsible for restenosis after PTCA are not completely understood but may be caused by complex interplay among several different biological agents and pathways. It has been theorized that the etiology of the disease process includes: (1) a shift in smooth muscle phenotype from a quiescent, contractile state to a migrating, proliferative from; (2) migration of the transformed smooth muscle cell from the media to the intima; and (3) massive proliferation of smooth muscle cells in the intima. Investigations of the pathogenesis of intima thickening have produced a theory that, following arterial injury, platelets, endothelial cells, macrophages and smooth muscle cells release various cytokines such as interleukin-1 (1L-1) and paracrine and autocrine growth factors such as platelet derived growth factor, epidermal growth factor, insulin-like growth factor, and fibroblast growth factor. T-cells and macrophages also migrate into the neointima. This cascade of events, as it has been suggested, results in an excessive proliferation and migration of smooth muscle cells, which causes the narrowing of the blood vessel and the reduction of the flow of blood through the vessel.

No surgical intervention or post-surgical treatment, to date, has proven significantly effective in preventing restenosis. Treatment strategies have included repeat angioplasty remodeling or the implantation of stents. Stents are scaffoldings, usually cylindrical or tubular in shape, which function to physically hold open and, if desired, to expand the wall of the passageway. Typically stents are capable of being compressed, so that they can be inserted through small cavities via catheters, and then expanded to a larger diameter once they are at the desired location. Mechanical intervention via stents, although a significant innovation in the treatment of occlusive regions, has not reduced the development of restenosis.

Pharmaceutical agents have also been locally and systemically administered, concurrent with or following PTCA, in an attempt to inhibit smooth muscle cell hyper-proliferation. The pharmaceutical agents employed in an attempt to treat restenosis have shown some favorable result. However, there is a great need for better and more effective compounds, and methods of using the compounds, to inhibit smooth muscle cell hyper-proliferation for the effective treatment of restenosis.

SUMMARY OF THE INVENTION

A composition and method of using the composition to inhibit the activity of vascular smooth muscle cells is provided. The composition inhibits abnormal or inappropriate migration and proliferation of smooth muscle cells. In one embodiment, the composition is actinomycin D or analogs or derivatives thereof. In another embodiment, the composition can be a combination of actinomycin D, or analogs or derivatives thereof, and at least one bioactive agent.

In accordance with one embodiment, a method is provided for inhibiting restenosis of a blood vessel by administering to a mammal the composition of the invention. Restenosis can be caused by hyper-proliferation of smooth muscle cells which can be initiated as a result of vascular trauma associated with treatment procedures such as angioplasty, stent placement, or grafting. The composition can be administered locally, systemically, orally or parenterally. The administration can be before, during or after the occurrence of the vascular trauma. Local administration can be, for example, via catheters or implantable prostheses such as stents, grafts, and polymeric carriers. In one suitable embodiment, self-expandable stents can be used for delivering the composition.

In accordance with another embodiment, a medical device is provided comprising a prosthesis for implanting in a body passageway and actinomycin D, or analogs or derivatives thereof, carried by the prosthesis. The actinomycin D, or analogs or derivatives thereof, can be released from the prosthesis in the body passageway. Examples of the prosthesis can include balloon-expandable stents, self-expandable stents, grafts, polymeric carriers, and particles. A therapeutic agent can also be carried by the prosthesis and used in combination with the actinomycin D, or analogs and derivatives thereof. The prosthesis can have a micro-porous structure and/or the prosthesis can be coated with a polymeric layer such as an ethylene vinyl alcohol copolymer layer.

In accordance with another embodiment, a therapeutic method is provided for treating a mammalian blood vessel. The method comprises administering to a mammal actinomycin D, or analogs or derivatives thereof, and implanting a self-expandable stent at a selected region of the mammalian blood vessel. Actinomycin D, or analogs or derivatives thereof, induces positive remodeling of the internal elastic lamina of the blood vessel wall and in response the self-expandable stent increases is diameter as the internal elastic lamia is positively remodeled. The actinomycin D, or analogs or derivatives thereof, can be administered prior to, contemporaneously with, or subsequent to the implantation of the self-expandable stent. In one embodiment, the self-expandable stent is coated with a polymeric material and the actinomycin D, or analogs or derivatives thereof, is impregnated in the polymeric coating for sustained release. The self-expandable stent can also contain cavities for releasably containing the actinomycin D, or analogs or derivatives thereof.

In accordance with another embodiment, a method for positively remodeling a layer of a blood vessel wall is provided. Actinomycin D is administered to a blood vessel to positively remodel the layer of the blood vessel wall.

DETAILED DESCRIPTION OF THE EMBODIMENTS

FIG. 1 graphically depicts in vitro experimental data showing affects of actinomycin D, mitomycin and docetaxel on smooth muscle cell proliferation;

DETAIL DESCRIPTION OF THE EMBODIMENTS

Active Component and Method Of Delivery

Figure 1:
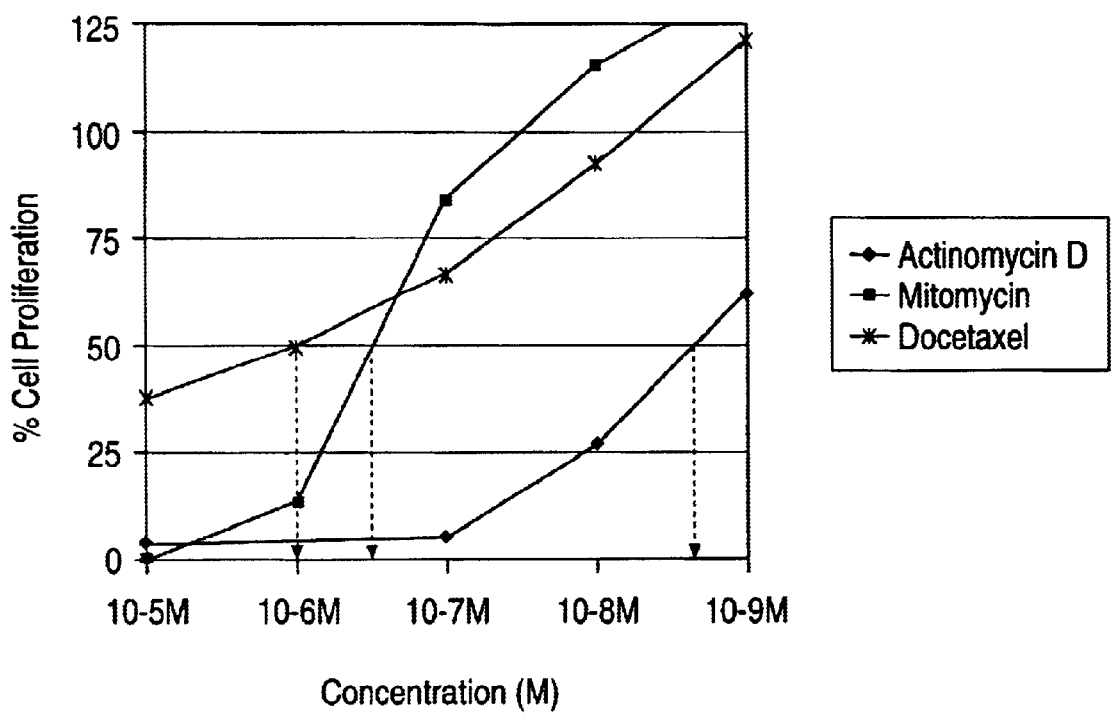

An active component and methods of using the active component for inhibiting the activity of vascular smooth muscle cells is provided. More specifically, the active component is aimed at inhibiting abnormal or inappropriate migration and/or proliferation of smooth muscle cells.

"Smooth muscle cells" include those cells derived from the medial and adventitia layers of the vessel which proliferate in intimal hyperplastic vascular sites following vascular trauma or injury. Under light microscopic examination, characteristics of smooth muscle cells include a histological morphology of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus.

"Migration" of smooth muscle cells means movement of these cells in vivo from the medial layers of a vessel into the intima, such as may also be studied in vitro by following the motion of a cell from one location to another, e.g., using time-lapse cinematography or a video recorder and manual counting of smooth muscle cell migration out of a defined area in the tissue culture over time.

"Proliferation+ of smooth musele cells means an increase cell number.

"Abnormal" or "inappropriate" proliferation means division, growth and/or migration of cells occurring more rapidly or to a significantly greater extent than typically occurs in a normally functioning cell of the same type, i.e., hyper-proliferation.

"Inhibiting" cellular activity means reducing, delaying or eliminating smooth muscle cell hyperplasia, restenosis, and vascular occlusions, particularly following biologically or mechanically mediated vascular injury or trauma or under conditions that would predispose a mammal to suffer such a vascular injury or trauma. As used herein, the term "reducing" means decreasing the intimal thickening that results from stimulation of smooth muscle cell proliferation. "Delaying" means retarding the progression of the hyper-proliferative vascular disease or delaying the time until onset of visible intimal hyperplasia, as observed, for example, by histological or angiographic examination. "Elimination" of restenosis following vascular trauma or injury means completely "reducing" and/or completely "delaying" intimal hyperplasia in a patient to an extent which makes it no longer necessary to surgically intervene, i.e., to re-establish a suitable blood flow through the vessel by, for example, repeat angioplasty, atheroectomy, or coronary artery bypass surgery. The effects of reducing, delaying, or eliminating restenosis may be determined by methods known to one of ordinary skill in the art, including, but not limited to, angiography, ultrasonic evaluation, fluoroscopy imaging, fiber optic visualization, or biopsy and histology. Biologically mediated vascular injury includes, but is not limited to injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia and irradiation. Mechanical mediated vascular injury includes, but is not limited to vascular injury caused by catheterization procedures or vascular scraping procedures such as percutaneous transluminal coronary angioplasty, vascular surgery, transplantation surgery, laser treatment, and other invasive procedures which disrupted the integrity of the vascular intima or endothelium. The active component of the invention is not restricted in use for therapy following vascular injury or trauma; rather, the usefulness of the component will also be determined by the component's ability to inhibit cellular activity of smooth muscle cells or to inhibit the development of restenosis.

In one embodiment, the active component is actinomycin D, or derivatives or analogs thereof (available from Sigma-Aldrich 1001 West Saint Paul Avenue, Milwaukee, Wis. 53233; or Cosmegen® available from Merck). Synonyms of actinomycin D include dactinomycin, actinomycin IV, actinomycin $I_1$, actinomycin $X_1$, and actinomycin $C_1$. Actinomycin D is represented by the molecular formula $C_{62}H_{86}N_{12}O_{16}$, and is generally depicted by the following structure:

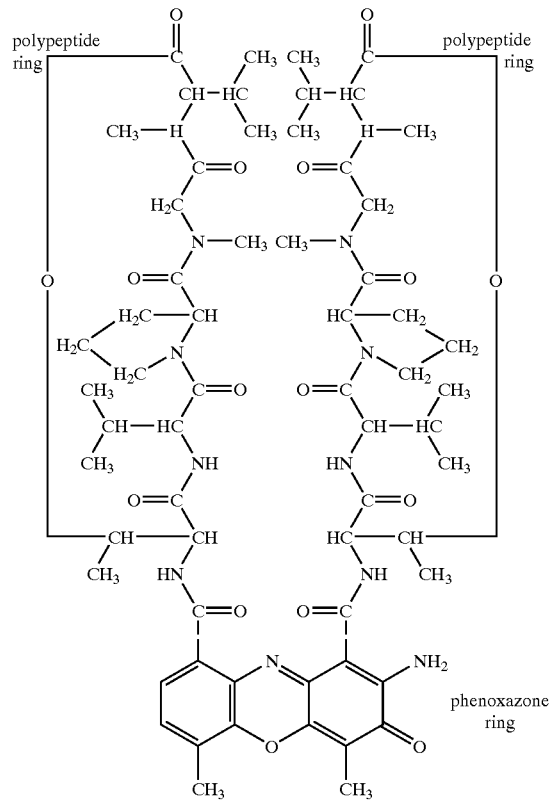

In an alternative embodiment, the active component is a cocktail combination of actinomycin D, or analogs or derivatives thereof, and a bioactive or therapeutic agent. The bioactive or therapeutic agent includes any substance capable of exerting a therapeutic or prophylactic effect in the practice of the present invention. The bioactive or therapeutic agents can also be for enhancing wound healing in a vascular site and improving the structural and elastic properties of the vascular site. Examples of such agents include other antiproliferative substances as well as antineoplastic, antiinflammatory, antiplatelet, anticoagulant, antifibrin, antithrombin, antimitotic, antibiotic, antioxidant, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck), calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

The active component, i.e., actinomycin D or analogs or derivatives thereof, alone or in cocktail formulation, can be formulated with a pharmaceutical carrier of solid or liquid form. A solid carrier can include one or more substances which may act as flavoring agents, lubricants, solubilizers, suspending agents, fillers, glidants, compression aids, binders or tablet-disintegrating agents. Additionally, the solid carrier can be an encapsulating material or a polymeric carrier for sustained delivery. In powder, the carrier is a finely divided solid which is in admixture with the finely divided active component. In tablets, the active component is mixed with a carrier having the necessary compression properties in suitable proportions and compacted in the shape and size desired. The powder and tablets can contain up to about 99% of the active component. Suitable solid carriers include, for example, calcium phosphate, magnesium stearate, talc, sugars, lactose, dexyin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active component can be dissolved or suspended in a pharmaceutically acceptable liquid carrier such as water or suitable organic solvents. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carrier for oral and parenteral administration include water, sucrose solution, lipid formulations, phosphate buffered saline solution, alcohols such as monohydric and polyhydric alcohols, and emulsions such as the oil-in-water or water-in-oil type. For parenteral adminstration, the carrier can also be an oily ester such as ethyl oleate and isopropyl myristate. The liquid carrier for pressurized compositions can be, for example, a halogenated hyrdrocarbon.

The administration of the active component can be accomplished systemically or locally. Systemic administration can be accomplished orally or parenterally including intravascularly, rectally, intranasally, intrabronchially, or transdermally. Liquid carriers which are sterile solutions or suspensions can be injected intramuscularly, intraperitoneally, subcutaneously, and intravenously. Rectal administration can be in the form of conventional suppository. For adminsitration by intranasal or intrabronchial inhalation or insufflation, the active component can be formulated into an aqueous or partially aqueous solution, which can then be utilized in the form of an aerosol. The active component can be administered transdermally through the use of a transdermal patch and a carrier that is inert to and mutually compatible with the active component, is non-toxic to the skin, and allows for the delivery of the active component for systemic absorption into the blood stream via the skin. The carrier may take any number of forms such as creams, ointments, pastes, and gels. The creams and ointments may be viscous liquids or semisolid emulsions of either the oil-in-water or water-in-oil type. Pastes made of absorptive powders dispersed in petroleum or hydrophilic petroleum containing the active component may also be suitable. Other devices capable of releasing the active component into the blood stream include semi-permeable membranes covering a reservoir containing the active component, with or without a carrier.

Local administration can be accomplished by a variety of techniques which administer the active component, i.e., actinomycin D, alone or in combination with other agents, at or near the target site. The following examples of local delivery techniques are provided for illustrative purposes and are not intended to be limiting. Examples include local delivery catheters, site specific carriers, implants, direct application, or direct injection. Local delivery by a catheter allows for the administration of the active component directly to the proliferative lesion. Local delivery by site specific carriers is conducted by attaching actinomycin D, or analogs or derivatives thereof, to a carrier which will direct or link the drug to the proliferative cells. Examples of this delivery technique include the use of carrier such as a protein ligand, a monoclonal antibody or a membrane anchored linker.

Local delivery by an implant is the placement of a matrix carrying the active component at the proliferative site. The matrix can release the active component by, for example, diffusion, degradation, chemical reaction, solvent activators, etc. One example of local delivery by an implant can include direct injection of vesicles or micro-particles into the proliferative site. These micro-particles may be composed of substances such as proteins, lipids, carbohydrates or synthetic polymers. The micro-particles can have the active component impregnated therein and/or coated thereon.

Yet in another example, a delivery system is provided in which a polymer that contains the active component is injected into the lesion in liquid form. The polymer can then be cured to form the implant in situ. In situ polymerization can be accomplished by photocuring or chemical reaction. Photocuring is conducted by mixing a polymer such as, but not limited to, acrylate or diacrylate modified polyethylene glycol (PEG), pluronic, polybutylene teraphthalate-co-polyethylene oxide, polyvinyl alcohol, hydroxy ethyl methacrylate (HEMA), hydroxy ethyl methacrylate-co-polyvinyl pyrrolidone, HEMA-co-PEG, or glycidol acrylate modified Heparin or sulfated dextran with the active component, with or without a photosensitizer (e.g., benzophenone) or a photoinitiator (e.g., 2,2 dimethoxy 2-phenyl acetophenone, and eosin-Y). The precursor system can be activated by a suitable wavelength of light corresponding to the system. The activation will result in a cured system that incorporates the active component.

Chemical reaction can be conducted by incorporating di-isocyanate, aldehyde, N-hydroxy succinimide, di-imidazole, —NH2, —COOH, with a polymer such as PEG or HEMA. The process of photocuring and chemical reaction is known to one of ordinary skill in the art.

Application via implants is not limited to the above described routes and other techniques such as grafts, micropumps or application of a fibrin glue or hydrogel containing the active component around the exterior of a designated region of the adventitia can also be implemented by one of ordinary skill in the art.

Local delivery by direct application includes the use of topical applications. An example of a local delivery by direct application is applying the active component directly to the arterial bypass graft during the surgical procedure. Another example of local delivery by direct application includes delivery of the active component into the pericardial sac as is known by one of ordinary skill in the art.

Local delivery by direct injection describes injecting a liquid carrier containing the active component directly into the proliferative site. The liquid carrier should be inert to and mutually compatible with the active component. The component can be in true solution or suspended in fine particles in the carrier. A suitable example of an inert carrier includes a sterile saline solution.

Systemic or local administration via the various disclosed routes may be continuous, intermittent, applied in a single treatment or multiple treatments. For example a regiment can be contemplated which involves a single dose given before and/or at the time of the treatment procedure, e.g., PCTA, and with a follow-up dose delivered after a predetermined time period subsequent to the treatment procedure. As another example, actinomycin D including any number of other suitable therapeutic agents can be administered in a single, sustained delivery treatment via a stent.

One of the aforementioned bioactive or therapeutic agents can also be administrated prior to, contemporaneously with, or subsequent to the administration of the active component. This can be accomplished via the same route or via mixed routes. For example, a vascular stent can be impregnated with actinomycin D and another therapeutic agent or combination of agents can be administered orally prior to the implantation procedure.

The dosage or concentration of the active component required to produce a favorable therapeutic effect should be less than the level at which the active component produces toxic effects and greater than the level at which non-therapeutic results are obtained. The dosage or concentration of the active component required to inhibit the desired cellular activity of the vascular region can depend upon factors such as the particular circumstances of the patient; the nature of the trauma; the nature of the therapy desired; the method of administration e.g., the binding affinity of the vascular smooth muscle cell bindingprotein; the time over which the active component administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Positive Remodeling and Self-expandable Prosthesis Therapy

Figure 3A:
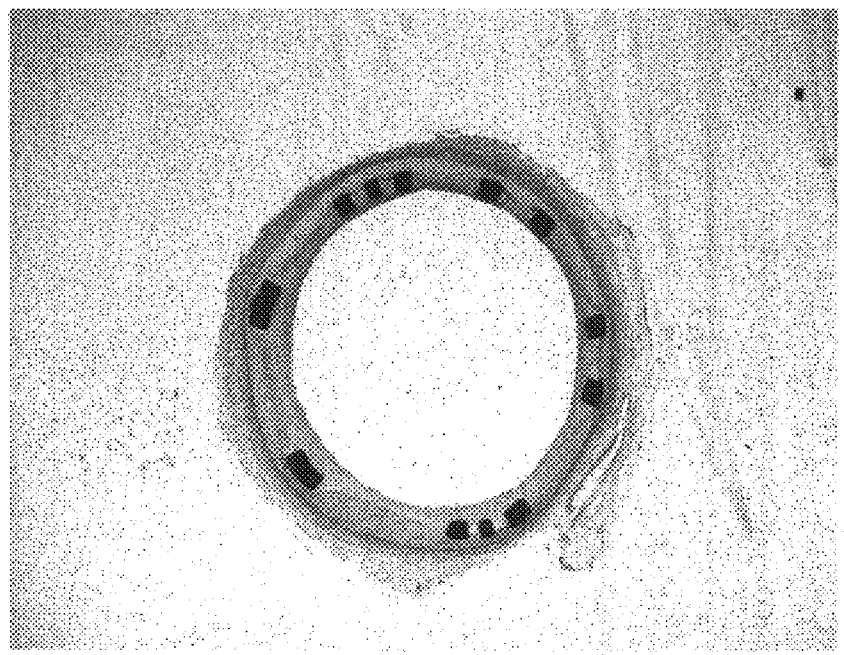
FIG. 3A is a picture of a histology slide of a coronary vessel from the control group in accordance with Example 3.
Figure 3B:
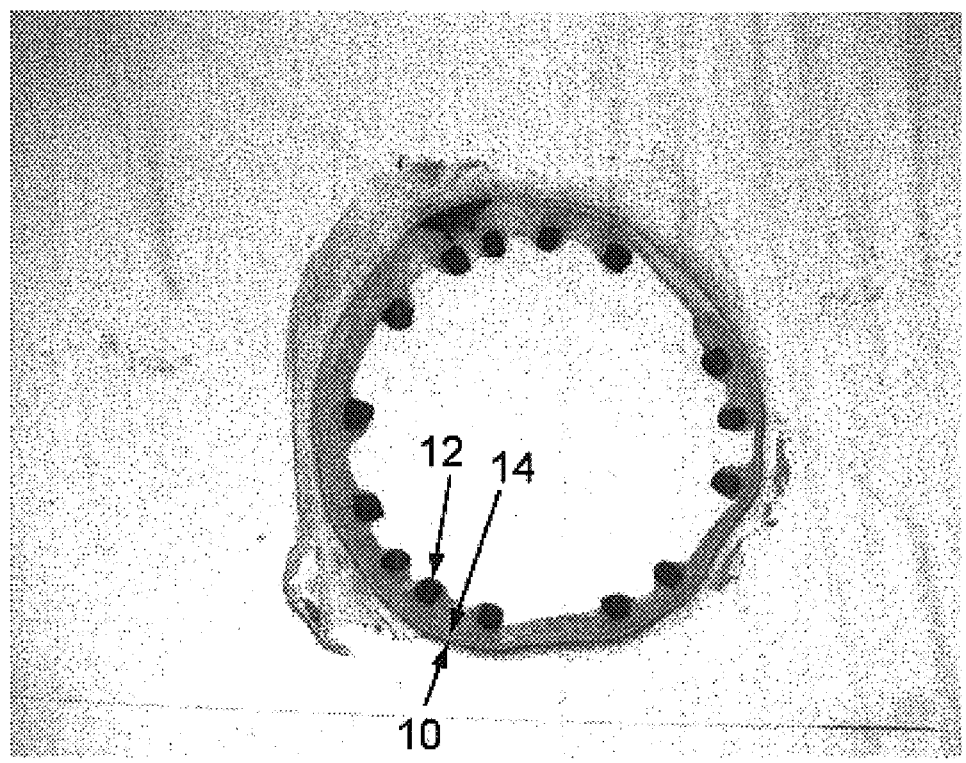
FIG. 3B is a picture of a histology slide of a coronary vessel from the actinomycin D group in accordance with Example 3.

Actinomycin D induces the positive remodeling of the vessel walls, more particularly positive remodeling of the external elastic lamina (EEL) of a blood vessel wall. Positive remodeling is generally defined as the ability of the vessel walls to structurally adapt, by increasing in lumen size, to chronic stimuli. A positively remodeled lumen wall has a greater diameter or size as compared to a lumen wall which has not been subjected to the remodeling effect. Accordingly, the flow of blood through the remodeled site is increased—flow which would have otherwise been reduced because of, for example, the presence of plaque build-up or migration and proliferation of cells. The index of remodeling is defined by the ratio of the area circumscribed by the EEL of the lesion site to the area circumscribed by the EEL of a reference site. As a result of the positive remodeling of the EEL, the internal elastic lamina (IEL), in response, can also increases in area or diameter. Actinomycin D, or analogs or derivative thereof, not only can inhibit abnormal or inappropriate migration and/or proliferation of smooth muscle cells, which can lead to restenosis, but can also induce positive remodeling of the blood vessel walls. Thus the widening of the diseased region becomes more pronounced. Positive remodeling of the vessel wall is illustrated by FIGS. 3A and 3B of EXAMPLE 3.

In one embodiment, a self-expandable stent can be implanted in conjunction with the actinomycin D therapy. Actinomycin D, or analogs or derivatives thereof, can be introduced prior to, contemporaneously with, or subsequent to the stent therapy. As the positive remodeling of the IEL occurs, the self-expandable stent increases in diameter to remain at the implantation site under self-fixation caused by permanent pressure or engagement against the inner wall of the vessel. The cross sectional area of the lumen, accordingly, is increased for the flow of blood.

In another embodiment, the self-expandable stent can be used for the local delivery of the active component. The self-expandable stent can include cavities, micro-depots or holes, reservoirs or a coating, such as a polymeric film layer, which can contain and release the active component by diffusion, degradation, desolution, chemical reaction, etc. The micro-depots or holes can be etched or created by a laser discharge. The polymeric coating can be any suitable polymeric compound that is mutually compatible with the active component. Suitable examples of polymeric compounds for the coating include, but are not limited to, polycaprolactone (PCL), poly-D,L-lactic acid (DL-PLA), poly-L-lactic acid (L-PLA), poly(lactide-co-glycolide), poly (hydroxybutyrate), poly(hydroxybutyrate-co-valerate), polydioxanone, polyorthoester, polyanhydride, poly (glycolic acid), poly(glycolic acid-co-trimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, aliphatic polycarbonates, fibrin, fibrinogen, cellulose, starch, collagen, parylene, PARYLAST (available from Advanced Surface Technology Product), polyurethane, polyethylene, polyethylene teraphthalate, ethylene vinyl acetate, silicone, polyethylene oxide, ethylene vinyl alcohol copolymer (commonly known by the generic name EVOH or by the trade name EVAL), and mixtures thereof.

EVOH possesses qualities that are desirable in stent coatings. Such qualities include, but are not limited to, susceptibility to expansion with the sent without any significant detachment from the surface of the stent; allowance for significant control of the release rate of the active component; and strong adherence to the surface of the stent, especially metallic material such as stainless steel. The self-expandable stent can be coated by any conventional method, such as by spraying the polymeric solution onto the surface of the stent or immersing the stent in the composition. By way of example, EVOH can be added to a dimethylsufoxide (DMSO) solvent followed by the addition of the active component to the blend. In this embodiment, the EVOH can include from about 0.1% to about 35%, usefully from about 12% to about 20% by weight of the total weight of the solution; the DMSO solvent can include from about 59.9% to about 99.8%, usefully from about 79% to about 87% by weight of the total weight of the solution; and the active component can include from about 0.1% to about 40%, usefully from about 1% to about 9% by weight of the total weight of the solution. In accordance with another embodiment the active component can be blended in a solution of EVOH, DMSO, and a wetting fluid. The inclusion of the wetting fluid results in the application of a more uniform coating. The suitable wetting fluid typically has a high capillary permeation and should have a viscosity not greater than bout 50 centipoise, usefully about 0.3 to about 5 centipoise, more narrowly about 0.4to about 2.5 centipoise. The wetting fluid should be mutually compatible with the other ingredients used in the formulation and should not precipitate the copolymer. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof. In this embodiment, the ethylene vinyl alcohol copolymer can include from about 0.1% to about 35%, usefully from about 10% to about 25% by weight of the total weight of the solution; the DMSO solvent can include from about 19.8% to about 98.8%, usefully from about 49% to about 79% by weight of the total weight of the solution; the wetting fluid can include from about 1% to about 80%, usefully from about 5% to about 40% by weight of the total weight of the solution; and the active component can include from about 0.1% to about 40%, usefully from about 1% to about 9% by weight of the total weight of the solution.

The type, structure, and material from which a self-expandable stent is made from are not of critical importance such that any suitable style can be selected by one of ordinary skill in the art. Briefly, a self-expandable stent includes a cylindrical body structure that has an outwardly directed bias which causes the cylindrical body to press radially against the inner wall of the vessel when the stent is released. The vessel wall provides a constraint for preventing the self-expanding stent from further increasing in diameter. The self-expandable stent remains at the implantation site under self-fixation caused by permanent pressure or engagement against the inner wall of the vessel. Desirably, such pressure has to be sufficiently large enough to keep the previous restriction open for the flow of blood. The diameter of the cylindrical body in a fully expanded state should be at least slightly larger than the inner diameter of the vessel in which the stent is deployed. Selection of amount of radial pressure and the expanded diameter of the stent can be determined one of ordinary skill in the art and are dependent on a variety of factors such as the severity of the occluded region and the inner diameter of the vessel wall.

The invention will be better understood by making reference to the following examples which are being provided by way of illustration and are not intended to unduly limit the scope of the present invention. The effect of actinomycin D to control cellular proliferation and intimal thickening is demonstrated by in vitro and in vivo studies.

EXAMPLE 1

Inhibition of SMC Proliferation With Actinomycin D

Medial smooth muscle cells (SMC) were isolated from rat aorta and cultured according to explant methods known to one of ordinary skill in the art. Cells were harvested via trypsinization and subcultivated. Cells were identified as vascular SMC through their characteristic hill-and-valley growth pattern as well as indirect immunofluorescence with monoclonal anti SMC α-actin. Studies were performed with cells at passage 3–4. SMC monlayers were established on 24 well culture dishes, scrape wounded and treated with actinomycin D, mytomycin and docetaxel. The cells were exposed to the drug solution of different concentrations for 2 hours and then washed with buffered saline solution. The proliferation of the cells was quantified by standard technique of thymidine incorporation. The results from the study are tabulated in FIG. 1.

The $IC_{50}$ (concentration at which 50% of the cells stop proliferating) of actimomycin D was $10^{-9}M$ as compared to $5\times10^{-5}M$ for mitomycin and $10^{-6}M$ for docetaxel. Actinomycin D was the most potent agent to prevent SMC proliferation as compared to other pharmaceutical agents.

EXAMPLE 2

Reduction in Restenosis in the Porcine Coronary Artery Model

Porcine coronary models were used to assess the degree of the inhibition of neointimal formation in the coronary arteries of a porcine stent injury model by Actinomycin D, delivered with a microporous balloon catheter ($1\times10^6$ pores/$cm^2$ with size ranging from 0.2–0.8 micron).

The preclinical animal testing was performed in accordance with the NIH Guide for Care and Use of Laboratory Animals. Domestic swine were utilized to evaluate effect of the drug on the inhibition of the neointimal formation. Each testing procedure, excluding the angiographic analysis at the follow-up endpoints, was conducted using sterile techniques. During the study procedure, the activated clotting time (ACT) was monitored regularly to ensure appropriate anticoagulation. Base line blood samples were collected for each animal before initiation of the procedure. Quantitative coronary angiographic analysis (QCA) and intravascular ultrasound (IVUS) analysis was used for vessel size assessment.

The vessels at the sites of the delivery were denuded by inflation of the PTCA balloons to 1:1 balloon to artery ratio and moving the balloons back and forth 5 times. Actinomycin D was delivered to the denuded sites at 3.5 atm (3.61 kg/sq. cm) for 2 minutes using the microporous balloon catheters before stent deployment. The average volume of delivery was about 3.3+/−1.2 ml. Following drug delivery, stents were deployed at the delivery site such that final stent to artery ratio was 1.1:1.

QCA and IVUS analyses were used for stent deployment guidance. Pre-stenting IVUS measurements of the lumen size at the targeted vessel sites were performed for determination of the balloon (size) inflation pressure. Quantitative analysis of the stented coronary arteries to compare pre-stenting, post-stenting, follow-up minimal luminal diameters, stent recoil, and balloon/stent to artery ratio were performed. Following stent implantation and final angiogram, all devices were withdrawn and the wounds closed; the animals were allowed to recover from anesthesia as managed by the attending veterinarian or animal care professionals at the research center.

Upon return to the research laboratory at the 28-day endpoint, angiographic assessments were performed. Coronary artery blood flow was assessed and the stented vessels were evaluated to determine minimal lumen diameter. The animals were euthanized following this procedure at the endpoint. Following euthanasia, the hearts were pressure perfusion fixed with formalin and prepared for histological analysis, encompassing light microscopy, and morphometry. Morphometric analysis of the stented arteries included assessment of the position of the stent struts and determination of vessel/lumen areas, percent (%) stenosis, injury scores, intimal and medial areas and intima/media ratios. Percent stenosis is quantitated by the following equation:

$$100 \, (IEL \, area - lumen \, area)/IEL \, area$$

where IEL is the internal elastic lamia.

Figure 2A:
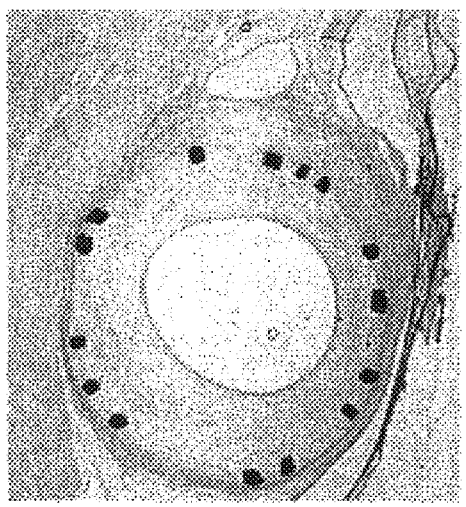
FIG. 2A is a picture of a histology slide of a coronary vessel from the control group in accordance with Example 2.
Figure 2B:
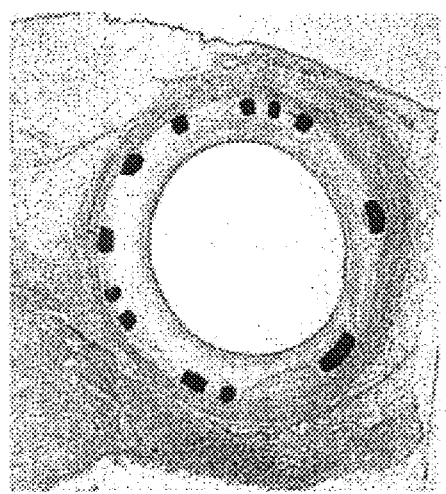
FIG. 2B is a picture of a histology slide of a coronary vessel from the actinomycin D group in accordance with Example 2.

The control group of animals received delivery of water instead of the drug. group of animals received actinomycin D in two different concentration of $10^{-5}M$ and $10^{-4}M$. The results of the study are tabulated in Table 1. The percent stenosis in the treated groups (32.3+/−11.7) was significantly decreased as compared to the control groups (48.8+/−9.8). FIGS. 2A and 2B illustrate sample pictures of the histology slides of the coronary vessels from the control and the Dose 1 group, respectively.

TABLE 1

| | CONTROL 0M | DOSE 1 1E-05M | DOSE 2 1E-04M | t test (significant if $p < 0.05$) | |
|---|---|---|---|---|---|
| | (n = 9) | (n = 10) | (n = 7) | p~ | p* |
| | ANGIOGRAPHIC DATA (QCA) | | | | |
| Percent Diameter Stenosis | 48.8 +/− 9.8 | 36.8 +/− 9.7 | 32.3 +/− 11.7 | 0.02 | 0.01 |
| | (n = 27) | (n = 30) | (n = 21) | p~ | p* |
| | HISTOMORPHOMETRIC DATA | | | | |
| Percent Stenosis (IEL area−lumen area)/IEL area | 63.4 +/− 12.7 | 51.8 +/− 13.8 | 54.1 +/− 11.7 | 0.002 | 0.01 |
| Residual Lumen | 0.36 +/− 0.16 | 0.49 +/− 0.14 | 0.46 +/− 0.08 | 0.002 | 0.01 |

TABLE 1-continued

| | CONTROL 0M | DOSE 1 1E-05M | DOSE 2 1E-04M | t test (significant if $p < 0.05$) | |
|---|---|---|---|---|---|
| (Lumen area)/ IEL area | | | | | |

~comparison between control and Dose 1
*comparison between control and Dose 2

The results of the in vitro and in vivo standard test procedures demonstrate that actinomycin D is useful for the treatment of hyper-proliferative vascular disease. Specifically, actinomycin D is useful for the inhibition of smooth muscle cell hyperplasia, restenosis and vascular occlusion in a mammal, particularly occlusions following a mechanically mediated vascular trauma or injury.

EXAMPLE 3

In vivo data is provided illustrated positive remodeling caused by the application of actinomycin D. Stents coated with EVAL impregnated with actinomycin D and a control group of stents coated with EVAL free from actinomycin D were implanted in porcine coronary arteries. The animals were sacrificed at the end of 28 days. The EEL area of the actinomycin D-loaded vessels was statistically significantly greater than the EEL area of the control vessels. The index of remodeling was 1.076 (8.54/7.94).

| Condition | Mean Area | Std Dev |
|---|---|---|
| IEL | | |
| Drug coated(Act-D in EVAL) | 7.47 | 0.89 |
| Control (EVAL) | 6.6 | 0.61 |
| p value | 0.0002 | Statistical significant difference |
| EEL (external elastic lamia) | | |
| Drug coated(Act-D in EVAL) | 8.54 | 0.87 |
| Control (EVAL) | 7.94 | 0.73 |
| p value | 0.014 | Statistical significant difference |

| EEL Area (mm$^2$) | | | | | |
|---|---|---|---|---|---|
| ID # | Control | ID # | Actinomycin D | ID # | EVAL |
| 48 LCX d | 6.3966 | 63 LCX d | 7.4498 | 63 LAD d | 8.3037 |
| 48 LCX m | 7.4601 | 63 LCX m | 8.2509 | 63 LAD m | 8.8545 |
| 48 LCX p | 7.3063 | 63 LCX p | 7.7342 | 63 LAD p | 9.4698 |
| 49 LAD d | 8.5573 | 63 RCA d | 7.9207 | 64 LCX d | 7.8063 |
| 49 LAD m | 8.5187 | 63 RCA m | 6.9928 | 64 LCX m | 7.1117 |
| 49 LAD p | 6.6346 | 63 RCA p | 8.3883 | 64 LCX p | 7.2411 |
| 58 LAD d | 8.6078 | 65 LAD d | 7.8546 | 64 RCA d | 8.3383 |
| 58 LAD m | 8.1674 | 65 LAD m | 9.2545 | 64 RCA m | 8.0793 |
| 58 LAD p | 8.3775 | 65 LAD p | 9.2515 | 64 RCA p | 8.3652 |
| 59 LCA d | 8.3054 | 68 LAD d | 8.7854 | 65 LCX d | 6.4638 |
| 59 LCX m | 7.3713 | 68 LAD m | 9.5164 | 65 LCX m | 7.1493 |
| 59 LCX p | 7.8662 | 68 LAD p | 9.1504 | 65 RCA d | 8.5955 |
| 59 RCA d | 7.3714 | 69 LCX d | 9.6679 | 65 RCA m | 8.0855 |
| 59 RCA m | 6.6783 | 69 LCX m | 9.1237 | 65 RCA p | 8.4785 |
| 59 RCA p | 7.4707 | 69 LCX p | 9.9849 | 68 LCX d | 8.4723 |

-continued

| | | | | | |
|---|---|---|---|---|---|
| 62 LCX d | 7.8784 | 69 RCA d | 9.4765 | 68 LCX m | 7.8382 |
| 62 LCX m | 7.5318 | 69 RCA m | 7.4424 | 68 LCX p | 8.0570 |
| 62 LCX p | 6.2647 | 69 RCA p | 9.1462 | 68 RCA d | 8.4840 |
| 62 RCA d | 8.3240 | 70 LCX d | 8.9504 | 68 RCA p | 8.8767 |
| 62 RCA m | 7.9535 | 70 LCX m | 8.9117 | 69 LAD d | 6.6648 |
| 62 RCA p | 8.5454 | 70 LCX p | 8.7533 | 69 LAD m | 6.8614 |
| 67 LAD d | 8.9532 | 70 RCA d | 7.3249 | 69 LAD p | 7.7632 |
| 67 LAD m | 9.2410 | 70 RCA m | 7.1061 | 70 LAD d | 7.5175 |
| 67 LAD p | 8.3841 | 70 RCA p | 8.5830 | 70 LAD m | 7.8630 |
| | | | | 70 LAD p | 8.2222 |
| AVG | 7.8402 | | 8.5425 | | 7.9475 |
| SD | 0.8046 | | 0.8755 | | 0.7349 |

ActD vs EVAL

| | |
|---|---|
| p = | 0.014709 |
| AVG % EEL growth | 7.486304 |

IEL Area (mm2)

| ID # | Control | ID # | Actinomycin D | ID # | EVAL |
|---|---|---|---|---|---|
| 48 LCX d | 5.2178 | 63 LCX d | 6.3785 | 63 LAD d | 6.9687 |
| 48 LCX m | 6.2108 | 63 LCX m | 7.5206 | 63 LAD m | 7.3908 |
| 48 LCX p | 6.1125 | 63 LCX p | 6.9992 | 63 LAD p | 7.3563 |
| 49 LAD d | 7.2848 | 63 RCA d | 6.9632 | 64 LCX d | 6.4420 |
| 49 LAD m | 7.4117 | 63 RCA m | 6.0418 | 64 LCX m | 6.0064 |
| 49 LAD p | 5.9918 | 63 RCA p | 7.4794 | 64 LCX p | 5.9970 |
| 58 LAD d | 7.2049 | 65 LAD d | 6.2324 | 64 RCA d | 6.8001 |
| 58 LAD m | 6.9334 | 65 LAD m | 8.3785 | 64 RCA m | 6.8561 |
| 58 LAD p | 6.9454 | 65 LAD p | 8.5819 | 64 RCA p | 7.0172 |
| 59 LCA d | 7.2640 | 68 LAD d | 8.0964 | 65 LCX d | 5.2485 |
| 59 LCX m | 6.2014 | 68 LAD m | 8.6879 | 65 LCX m | 6.1135 |
| 59 LCX p | 6.7283 | 68 LAD p | 8.0914 | 65 RCA d | 7.1525 |
| 59 RCA d | 6.0519 | 69 LCX d | 8.7181 | 65 RCA m | 6.4815 |
| 59 RCA m | 5.9992 | 69 LCX m | 8.0273 | 65 RCA p | 7.1775 |
| 59 RCA p | 5.9032 | 69 LCX p | 8.5222 | 68 LCX d | 6.9571 |
| 62 LCX d | 6.5329 | 69 RCA d | 8.3796 | 68 LCX m | 6.5724 |
| 62 LCX m | 6.2804 | 69 RCA m | 6.4219 | 68 LCX p | 6.7740 |
| 62 LCX p | 4.9303 | 69 RCA p | 7.7757 | 68 RCA d | 7.2425 |
| 62 RCA d | 7.0977 | 70 LCX d | 7.5392 | 68 RCA p | 7.5554 |
| 62 RCA m | 6.7466 | 70 LCX m | 7.6573 | 69 LAD d | 5.5505 |
| 62 RCA p | 7.1747 | 70 LCX p | 6.9749 | 69 LAD m | 5.5571 |
| 67 LAD d | 8.0264 | 70 RCA d | 6.2815 | 69 LAD p | 6.2697 |
| 67 LAD m | 8.1144 | 70 RCA m | 5.9760 | 70 LAD d | 6.3212 |
| 67 LAD p | 7.2091 | 70 RCA p | 7.6195 | 70 LAD m | 6.6518 |
| | | | | 70 LAD p | 6.9032 |
| AVG | 6.6489 | | 7.4727 | | 6.6025 |
| SD | 0.7883 | | 0.8972 | | 0.6130 |

ActD vs EVAL

| | |
|---|---|
| p = | 0.000283 |
| AVG % IEL growth | 13.17981 |

FIGS. 3A and 3B illustrate sample pictures of the histology slides of the coronary vessels from the control group 64 RCA (Right Coronary Group) and the actinomycin D loaded stent group 68 LAD (Left Anterior Descending), respectively. The stent used was an Advanced Cardiovascular Systems Multi-Link Duet™ (stainless steel). As is illustrated by FIG. 3B, the positive remodeling of IEL 10, caused by the application of actinomycin D, creates a gap between stent struts 12 and IEL 10. Thrombus deposits, illustrated by reference number 14, are formed in the gap over time. The use of a self-expandable stent eliminates the formation of the gap as the stent self-expands in response to the positive remodeling of IEL. Thrombus deposits can be, accordingly, eliminated.

EXAMPLE 4

Multi-Link Duet™ stents (available from Guidant corporation) are cleaned in an if ultrasonic bath of isopropyl alcohol for 20 minutes, then air dried. An EVOH stock solution is made having an EVOH:DMSO ratio of 1:4. The mixture is placed in a warm water shaker bath at 60° C. for 12 hours. The solution is mixed, then cooled to room temperature. A 9% by weight actinomycin D solution is formulated as follows: 2.96 grams of the EVOH:DMSO solution is mixed with 0.29 grams of actinomycin D, then 0.9 grams of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. From about 0.05 to about 100 microgams/mm $^2$ of actinomycin D can be carried by the stent. More specifically, ranges from about 0.5 to about 20 micrograms/mm$^2$ and from about 2.5 to about 15 micrograms/mm$^2$ can also be suitable.

EXAMPLE 5

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 5.06% by weight actinomycin D solution was formulated as follows: 40 milligrams of actinomycin D was dissolved in 150 milligrams of THF, then 600 milligrams of the EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 260 micrograms and an average actinomycin D loading of about 64 micrograms was achieved. The coating was transparent, giving the stents a glossy-like shine.

EXAMPLE 6

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 3.75% by weight actinomycin D solution was formulated as follows: 60 milligrams of actinomycin D was dissolved in 310 milligrams of DMF, then 1.22 grams of EVOH:DMSO solution was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 270 micrograms with an average actinomycin D content of about 51 micrograms was achieved. The coating was transparent, giving the stents a glossy-like shine.

EXAMPLE 7

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 6.1% by weight actinomycin D solution was formulated as follows: 100 milligrams of actinomycin D was dissolved in 310 milligrams of DMF, then 1.22 grams of EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 250 micrograms and an average actinomycin D loading of about 75 micrograms was achieved.

EXAMPLE 8

Multi-Link Duet™ stents are cleaned in an ultrasonic bath of isopropyl alcohol for 20 minutes, then air dried. An EVOH stock solution is made having an EVOH:DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVOH:DMSO solution is mixed with 40 milligrams of actinomycin D, then 2000 milligrams of THF is added. The cleaned Multi-Link Due™ stents can be sprayed upon by the above formulation. The coated stents are cured in a forced air convection oven 60° C. for 15 minutes. Additional layers of the coating are applied and cured in the above manner. The final curing step for the coated stents is conducted for about 4 hours.

While the particular embodiments of the present invention have been shown and described, it will be obvious to those skilled in the art that changes and modifications can be made without departing from this invention in its broader aspect and, therefore, the appended claims are to encompass within their scope all such changes and modifications as fall within the true spirit and scope of this invention.

What is claimed is:

1. A therapeutic method for positively remodeling a mammalian blood vessel, comprising:
    (a) administering to a mammal actinomycin D, or analogs or derivatives thereof; and
    (b) implanting a self-expandable stent at a selected region of the mammalian blood vessel, wherein the actinomycin D, or analogs or derivatives thereof, induces positive remodeling of the blood vessel wall.

2. The method of claim 1, wherein the self-expandable stent has an inner diameter after implantation, and wherein the inner diameter of the self-expandable stent increases as the vessel wall is positively remodeled.

3. The method of claim 1, wherein the actinomycin D, or analogs or derivatives thereof, inhibits abnormal or inappropriate migration or proliferation of smooth muscle cells.

4. The method of claim 1, wherein the actinomycin D, or analogs or derivatives thereof, is administered prior to, contemporaneously with, or subsequent to the implantation of the self-expandable stent.

5. The method of claim 1, wherein the administration of the actinomycin D, or analogs or derivatives thereof, is systemic or local.

6. The method of claim 1, wherein the administration of the actinomycin D, or analogs or derivatives thereof, is oral or parenteral.

7. The method of claim 1, wherein the self-expandable stent is coated with a polymeric material, the actinomycin D, or analogs or derivatives thereof, being impregnated in the polymeric material for sustained release.

8. The method of claim 7, wherein the polymeric material is ethylene vinyl alcohol copolymer.

9. The method of claim 1, wherein a surface of the self-expandable stent contains cavities, the cavities releasably containing the actinomycin D, or analogs or derivatives thereof.

10. A therapeutic method for positively remodeling a mammalian blood vessel, comprising:
    (a) inhibiting restenosis of a blood vessel by administering to a mammal actinomycin D or analogs or derivatives thereof; and
    (b) delivering a self-expanding implantable prosthesis to a selected region of a mammalian blood vessel, the implantable prosthesis comprising a body having a plurality of struts, wherein the actinomycin D, or analogs or derivatives thereof, induces positive remodeling of the wall of the blood vessel.

11. The method of claim 10, wherein an effective amount of actinomycin D, or analogs or derivatives thereof, is administered which inhibits abnormal or inappropriate migration or proliferation of smooth muscle cells.

12. The method of claim 10, wherein the administration is selected from the group consisting of local and systemic routes.

13. The method of claim 10, wherein the administration is selected from the group consisting of oral and parenteral routes.

14. The method of claim 10, wherein the administration is via a catheter.

15. The method of claim 10, wherein the implantable prosthesis is a self-expandable stent.

16. The method of claim 10, wherein the administration is via a polymeric carrier.

17. The method of claim 12, wherein the implantable prosthesis is a self-expandable stent, and wherein the stent is coated with a polymeric carrier impregnated with the actinomycin D, or analogs or derivatives thereof.

18. The method of claim 12, additionally comprising administering at least one therapeutic agent in combination with the actinomycin D, or analogs or derivatives thereof, to the mammal.

19. The method of claim 18, wherein the therapeutic agent is administered before, during or after the administration of the actinomycin D, or analogs or derivative thereof.

20. The method of claim 12, wherein the restenosis is the result of a vascular trauma associated with angioplasty, placement of a stent, or grafting, and wherein the actinomycin D, or analogs or derivatives thereof, is locally administered to a designated region of the blood vessel for a predetermined duration of time subsequent to the vascular trauma.

21. The method of claim 12, wherein the restenosis is the result of a vascular trauma and wherein the actinomycin D, or analogs or derivatives thereof, is administered before, during, or after the occurrence of the vascular trauma.

22. A method for positively remodeling a blood vessel, comprising inserting an expandable prosthesis carrying actinomycin D, or analogs or derivatives thereof, in a selected region of the blood vessels wherein the actinomycin D, or analogs or derivatives thereof, is discharged to positively remodel the blood vessel.

23. The method of claim 22, wherein the external elastic lamina of the blood vessel is positively remodeled.

24. The method of claim 22, wherein the prosthesis is a self-expandable stent.

25. The method of claim 22, wherein the prosthesis is a self-expandable stent coated with a polymeric material, the actinomycin D, or analogs or derivatives thereof, being impregnated in the polymeric material.

26. The method of claim 22, wherein the prosthesis additionally carries at least one therapeutic agent used in combination with the actinomycin D, or analogs or derivatives thereof.

27. The method of claim 26, wherein the therapeutic agent is paclitaxel or docetaxel.

28. A method for positively remodeling a layer of a blood vessel wall, comprising:

administering to a blood vessel actinomycin D, or analogs or derivatives thereof, the actinomycin D, or analogs or deriviatives thereof being carried by a self-expandable stent, wherein the layer of the blood vessel wall is positively remodeled.

* * * * *